US006413463B1

(12) United States Patent
Yamamoto et al.

(10) Patent No.: US 6,413,463 B1
(45) Date of Patent: Jul. 2, 2002

(54) PROCESS FOR PRODUCING HARD CAPSULE

(75) Inventors: Taizo Yamamoto, Osaka; Shunji Nagata, Ashiya; Seinosuke Matsuura, Kyoto, all of (JP)

(73) Assignee: Shionogi Qualicaps Co., Ltd., Yamatokoriyama (JP)

( * ) Notice: Subject to any disclaimer, the term of this patent is extended or adjusted under 35 U.S.C. 154(b) by 0 days.

(21) Appl. No.: 09/582,560

(22) PCT Filed: Oct. 25, 1999

(86) PCT No.: PCT/JP99/05874

§ 371 (c)(1),
(2), (4) Date: Jun. 29, 2000

(87) PCT Pub. No.: WO00/25760

PCT Pub. Date: May 11, 2000

(30) Foreign Application Priority Data

Oct. 29, 1998 (JP) ............................................. 10-308204

(51) Int. Cl.[7] ............................ A61K 9/48; B05D 1/18; B29C 41/14
(52) U.S. Cl. ....................................... 264/301; 424/451
(58) Field of Search .......................... 264/301; 424/451, 424/452, 456

(56) References Cited

U.S. PATENT DOCUMENTS

| 5,264,223 A | 11/1993 | Yamamoto et al. | ......... 424/451 |
| 5,431,917 A | 7/1995 | Yamamoto et al. | ......... 424/451 |
| 5,756,123 A | 5/1998 | Yamamoto et al. | ......... 424/451 |

FOREIGN PATENT DOCUMENTS

| EP | A1-714656 | 6/1996 |
| EP | B1-592130 | 4/1999 |
| JP | A-58138458 | 8/1983 |
| JP | A-3279325 | 12/1991 |
| JP | A-6116139 | 4/1994 |
| JP | A-8208458 | 8/1996 |

Primary Examiner—Leo B. Tentoni
(74) Attorney, Agent, or Firm—Birch, Stewart, Kolasch & Birch, LLP

(57) ABSTRACT

A method of manufacturing hard capsules is characterized by comprising the steps of dispersing a water-soluble cellulose derivative in hot water and cooling the dispersion to effect dissolution of the water-soluble cellulose derivative in the water, adding and dissolving a gelling agent in the water-soluble cellulose derivative solution to give a capsule-preparing solution, dipping a capsule-forming pin into the capsule-preparing solution at a predetermined temperature, then drawing out the pin and inducing gelation of the capsule-preparing solution adhering to the pin.

6 Claims, 1 Drawing Sheet

PROCESS FOR PRODUCING HARD CAPSULE

This application is the national phase under 35 U.S.C. §371 of PCT International Application No. PCT/JP99/05874 which has an International filing date of Oct. 25, 1999, which designated the United States of America.

TECHNICAL FIELD

The present invention relates to a method of manufacturing hard capsules based on a water-soluble cellulose derivative such as hydroxypropyl methyl cellulose (HPMC).

BACKGROUND ART

Hard capsules based on water-soluble cellulose derivatives such as HPMC are described in JP-A 3-279325. These hard capsules are obtained by the gelation of a water-soluble cellulose derivative such as HPMC using carrageenan as the gelling agent and using potassium ions or ammonium ions as gelling aids. The method of manufacture is comprised of preparing an aqueous capsule base solution containing the water-soluble cellulose derivative, the gelling agent and the gelling aid, dipping capsule-forming pins into the aqueous solution, then drawing the pins out of the solution and allowing the solution adhering to the outside surface of the pins to gel at room temperature so as to form a capsule film on the outside surface of the pin.

A specific method that is used involves dissolution of the gelling agent and the gelling aid in purified water at approximately 70° C. The water-soluble cellulose derivative is dispersed in the solution, following which the dispersion is cooled to from 50 to 52° C. The pins are dipped into the resulting solution, then drawn out to form capsules. If the temperature of the dipping solution falls outside the range of 50 to 52° C., the jelly-like viscosity of the solution undergoes a subtle change that prevents good adherence of the solution to the capsule-forming pins during dipping and makes it difficult to obtain a uniform capsule film.

The need for strict temperature control of the jelly at such a high temperature so as to obtain uniform capsules places a large burden on equipment and other resources. It is also troublesome to maintain tight control of the operation.

DISCLOSURE OF THE INVENTION

The invention has been made under the above-described circumstances, and its object is to provide a method of manufacturing hard capsules which is capable of producing uniform hard capsules made of a water-soluble cellulose derivative such as HPMC without requiring strict temperature control; that is, a method which allows some play in the temperature control.

To achieve the above object, the invention provides a method of manufacturing hard capsules, characterized by comprising the steps of dispersing a water-soluble cellulose derivative in hot water and cooling the dispersion to effect dissolution of the water-soluble cellulose derivative in the water, adding and dissolving a gelling agent in the water-soluble cellulose derivative solution to give a capsule-preparing solution, dipping a capsule-forming pin into the capsule-preparing solution at a predetermined temperature, then drawing out the pin and inducing gelation of the capsule-preparing solution adhering to the pin.

In the practice of the invention, the dispersion of a water-soluble cellulose derivative such as HPMC in hot water followed by cooling effects complete dissolution of the water-soluble cellulose derivative in the water. By also subsequently dissolving a gelling agent such as carrageenan, then dipping a pin therein typically at a temperature of 35 to 50° C. and drawing the pin out, good gelation of the capsule-preparing solution adhering to the pin is achieved.

More specifically, as discussed subsequently in Experiment, FIG. 1 is a graph of the relationship between the cooling and heating state of the HPMC solution and the solution viscosity. As shown in FIG. 1, when HPMC is dispersed in approximately 70° C. hot water, it substantially does not dissolve in the hot water, and the resulting HPMC dispersion has a very low viscosity. However, when the HPMC dispersion is cooled, the viscosity begins rising at a temperature of about 60 to 55° C. and reaches a maximum at a temperature of about 45 to 40° C. (line segment A in the graph). Note that no particular pH adjustment is carried out in FIG. 1. Since it is well-known that the viscosity of HPMC and other water-soluble cellulose derivatives is affected by such factors as the pH and ionic strength, the plot in FIG. 1 serves as one model.

Prior-art methods of manufacturing HPMC hard capsules involve adding and dispersing HPMC in approximately 70° C. water in which a gelling agent such as carrageenan and a gelling aid have already been dissolved, cooling the dispersion, dipping capsule-forming pins therein at a temperature of 52 to 50° C. during the rise in viscosity (indicated by "X" in the graph), and using both the gelling effect of the gelling agent brought about by subsequent cooling and the rise in viscosity of the HPMC to produce the capsules.

As noted above, after the maximum viscosity has been reached, the HPMC solution is cooled, whereupon the viscosity decreases as indicated by B in the diagram, generally resulting in complete dissolution in water at a temperature of 30 to 40° C. or lower. If heating is then carried out from a state where the HPMC is thoroughly dissolved in water, as shown by C in the diagram, the viscosity remains substantially unchanged up to about 45° C. Although not shown in the diagram, the viscosity begins to rise sharply at or above about 45 to 50° C. Carrageenan is added and dissolved at a temperature preceding the sharp rise in viscosity (e.g., at a temperature close to 40° C. indicated by "Y" in the diagram). In the diagram, the viscosity decreases with the addition of carrageenan. This is because the addition of a solution of carrageenan in water to the aqueous solution of HPMC dilutes the latter. When the aqueous HPMC solution containing a dissolved gelling agent is then cooled, the viscosity rises as shown by D in the diagram, with a particularly sharp rise in viscosity, namely gelation, occurring at about 35° C.

The method of the present invention carries out capsule production by making use of, in a viscosity change pattern like that shown in FIG. 1, cooling after the solution has reached maximum viscosity and dissolution of a water-soluble cellulose derivative such as HPMC in water, subsequent addition and dissolution of a gelling agent and dipping of a capsule-forming pin at a predetermined temperature, then a rise in viscosity and gelation of the water-soluble cellulose derivative solution containing the dissolved gelling agent in a cooling or heating step.

In the inventive method, because dipping of the pin can be carried out in a temperature region where the change in viscosity of the water-soluble cellulose derivative solution (jelly) is small, even if the pin dipping temperature differs somewhat from a predetermined temperature setting, very little if any change in the jelly viscosity arises. Thus, in addition to thorough and full dissolution of the water-soluble cellulose derivative in water, a uniform capsule can be stably and reliably produced without strict temperature control of the jelly, and even with some degree of latitude in temperature control. As a result, high-quality capsules can be obtained with relatively loose control of the operation.

Furthermore, in cases where foreign matter is removed from the water-soluble cellulose derivative solution by filtration, because this can be done at a low temperature, the operation is easy to carry out. In addition, the water-soluble cellulose derivative becomes completely dissolved at a low temperature, making it possible to reliably filter off foreign matter.

Moreover, by using a method in which the water-soluble cellulose derivative is dispersed in hot water, the dispersion is cooled, and a gelling agent is subsequently added, both new and old cellulose derivative, such as HPMC that has already been formed into capsules and fresh HPMC, can be uniformly dissolved and mixed. Because the capsule film produced from this type of jelly is uniform, capsules that have already been produced can be recycled and the water-soluble cellulose derivative re-used without compromising the quality of the resulting capsules.

BEST MODE FOR CARRYING OUT THE INVENTION

Figure 1:
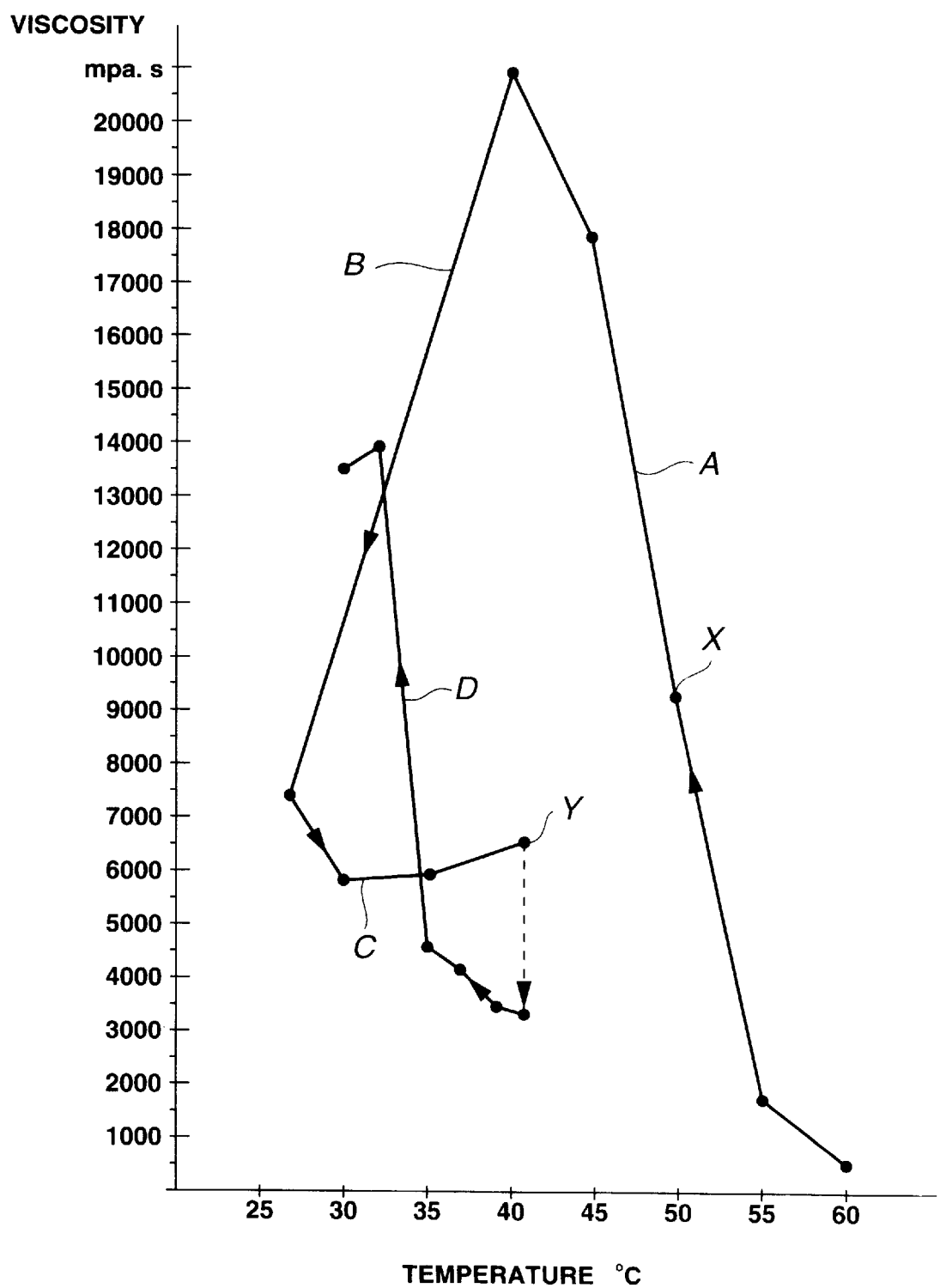
FIG. 1 is a graph showing the changes in viscosity that occur in a HPMC solution under cooling and heating.

The invention is described more fully below.

A water-soluble cellulose derivative and a gelling agent are used as the raw materials in the inventive method of manufacturing hard capsules.

Appropriate water-soluble cellulose derivatives are cellulose ethers substituted with alkyl groups, especially $C_1$ to $C_4$ lower alkyl groups, and/or hydroxylalkyl groups, especially $C_1$ to $C_4$ hydroxy-lower alkyl groups. Specific examples include hydroxypropyl methyl cellulose (HPMC), hydroxyethyl cellulose, hydroxypropyl cellulose and hydroxyethyl methyl cellulose. Particularly effective use can be made of a water-soluble cellulose derivative such as HPMC having a behavior in solution like that shown in FIG. 1 in which little change in viscosity occurs up to about 45 to 50° C. when the solution is reheated after having been cooled from an elevated temperature of at least 55° C. down to a temperature of 40° C. or less.

The gelling agent used may be any substance that induces the gelation of the water-soluble cellulose derivative. Suitable examples include carrageenan, tamarind seed polysaccharide, pectin, curdlan, gelatin, furcellaran, agar and gellan gum. Preferred gelling agents include carrageenan and gellan gum. These gelling agents may be used alone or as combinations of two or more thereof. The carrageenan may be, for example, κ-carrageenan or ι-carrageenan.

If necessary, a gelling aid may also be used. The gelling aid is selected according to the type of gelling agent. When κ-carrageenan is used as the gelling agent, the gelling aid used may be a water-soluble compound that provides potassium ions, ammonium ions or calcium ions, illustrative examples of which include potassium chloride, ammonium chloride, ammonium acetate and calcium chloride. When ι-carrageenan is used as the gelling agent, a water-soluble compound that provides calcium ions, such as calcium chloride, may be employed as the gelling aid.

For ease of operation and other reasons, the amount of water-soluble cellulose derivative used, given as the concentration in the capsule-preparing solution, is preferably from 10 to 35% by weight, and especially 18 to 28% by weight. The concentration of the gelling agent in the capsule-preparing solution is preferably 0.01 to 0.5% by weight, and especially 0.05 to 0.3% by weight. The concentration of the gelling aid in the capsule-preparing solution is preferably 0.05 to 0.6% by weight, and especially 0.06 to 0.2% by weight.

Additives ordinarily used in hard capsules, such as dyes and pigments may be suitably added in the practice of the invention.

In the inventive method, first of all the water-soluble cellulose derivative is dispersed in hot water. The temperature of the hot water may be selected as appropriate for the type of water-soluble cellulose derivative, although the temperature is preferably at least 55° C., more preferably from 60 to 85° C. and most preferably from 65 to 80° C. The water-soluble cellulose derivative is preferably poured and dispersed into hot water of a predetermined temperature within the above range. Alternatively, the water-soluble cellulose derivative may be poured into water having a temperature lower than this predetermined temperature, followed by heating to the predetermined temperature.

After the water-soluble cellulose derivative has been dispersed in hot water, the dispersion is cooled under stirring. Cooling may be carried out by either natural cooling or forced cooling, the aim in either case being the substantially complete dissolution of the water-soluble cellulose derivative in the water. The cooling temperature also is selected with this in mind. In general, cooling is carried out to preferably 35° C. or less, more preferably 30° C. or less, and most preferably room temperature (15 to 25° C.).

After dissolution of the water-soluble cellulose derivative has been effected by cooling, it is advantageous to filter the aqueous solution of water-soluble cellulose derivative so as to remove foreign matter such as solid impurities, then adjust the solution to a predetermined capsule-forming pin dipping temperature. The dipping temperature may be selected according to the type of water-soluble cellulose derivative, although heating to a temperature from higher than 35° C. to 50° C. is preferable, heating to a temperature from higher than 35° C. to 45° C. is more preferable, and heating to a temperature within a range of 38 to 43° C. is most preferable. Heating to a temperature which is too high may result in a sharp rise in the viscosity of the water-soluble cellulose derivative solution. To keep this undesirable effect from arising, the upper limit in the dipping temperature is set to a temperature which precedes the sharp rise in viscosity.

In the practice of the invention, the gelling agent is added and dissolved in the water-soluble cellulose derivative solution after the above cooling step. There is no particular limitation on the time of such addition, so long as addition is carried out after cooling and before or during temperature elevation of the water-soluble cellulose derivative solution. However, addition just before the solution temperature is raised to the capsule-forming pin dipping temperature or just after this temperature has been reached is preferred.

Addition of the gelling agent in the form of a solution thereof in water to the water-soluble cellulose derivative solution is preferable for achieving easy and uniform dissolution of the gelling agent, although in some cases the gelling agent may be added directly to the water-soluble cellulose derivative solution without first dissolving it in water.

A capsule-forming pin is dipped at the above-indicated dipping temperature into the capsule-preparing solution (jelly solution) obtained as just described by adding and dissolving the gelling agent in the water-soluble cellulose derivative solution. The pin is then drawn out, and the capsule-preparing solution adhering to the pin is subjected to gelation and drying, giving a hard capsule.

Gelation is preferably achieved by cooling on standing. However, in cases where the capsule-preparing solution attains a high viscosity and gels under heating, gelation may be effected by heating to a temperature of 50 to 80° C., for example, after the pin has been drawn out.

The viscosity of the capsule-preparing solution (jelly solution) is not subject to any particular limitation, although it is preferably set within a range of 100 to 10,000 mPa·s, and especially 1,000 to 8,000 mPa·s, at the capsule dipping temperature. This viscosity is the value obtained using a Brookfield-type rotational viscometer. Too low a viscosity results in the adherence of too little capsule-preparing solution to the pin, giving a capsule film of insufficient thickness. On the other hand, control of the capsule shape becomes difficult if the viscosity is too high.

If necessary, additives such as gelling aids, dyes and pigments may be incorporated into the capsule-preparing solution. These ingredients may be added at any stage. For example, they may be added to the hot water, or at the time of gelling agent addition.

Capsules produced by the method of the invention may be used in drug and food products, and also in other applications including chemicals for use on animals and plants, and fertilizers. Drug applications include oral medications, containers for inhalants, and suppositories. The capsules can also be used as so-called quasi-pharmaceuticals for such purposes as disinfecting and cleaning dentures, eyeglasses and contact lenses.

Specific examples of ingredients that may be filled into HPMC hard capsules include commonly known powders, granules and tablets, and also alcohols, including polyhydric alcohols such as stearyl alcohol, cetanol, and polyethylene glycol 600, 800, 1000, 1500, 2000, 3000, 4000, 6000, 8000 and 20000; fats and oils such as sesame oil, soybean oil, peanut oil, corn oil, hardened oil, paraffin oil and white beeswax; and fatty acids and fatty acid derivatives such as stearic acid, palmitic acid, myristic acid, triethyl citrate, triacetine and middle-chain fatty acid triglycerides. Physiologically active substances that may be used to fill capsules produced according to the inventive method for drug and food applications are not subject to any particular limitation so long as they are non-toxic. The capsules may be filled with a very broad range of drugs, including vitamins, antipyretics, analgesics, anti-inflammatory agents, antiulceratives, cardiotonics, anticoagulants, hemostatics, bone resorption inhibitors, vascularization inhibitors, antidepressants, antineoplastics, antitussive expectorants, muscle relaxants, anticonvulsants, antiallergics, antiarrhythmics, vasodilators, hypotensive diuretics, diabetes medications, antitubercular agents, hormones and narcotic antagonists.

Examples of suitable vitamins include vitamin A, vitamin $B_1$, vitamin $B_2$, vitamin $B_6$, vitamin $B_{12}$, nicotinamide, calcium pantothenate, vitamin C, vitamin $D_2$, vitamin E and vitamin K.

Additional examples of suitable drug substances include ethyl eicosapentaenoate, actinomycin D, acyclovir, azimexon, aspirin, aztreonam, acetazolamide sodium, acetaminophen, acetohexamide, acetomenaphthon, adrenochrome monoaminoguanidine methanesulfonic acid, amikacin, ε-aminocaproic acid, aminophylline, alprostadil, allylisopropylacetylurea, altretamine, amfenac, ampicillin, isoniazid, isopropylantipyrine, ibuprofen, ifosfamide, imipramine, indomethacin, urinastatin, ethosuximide, emedastine enanthate, estriol, erythromycin, ethambutol, tubocurarine chloride, alprenolol hydrochloride, alloclamide hydrochloride, isoproterenol hydrochloride, etilefrin hydrochloride, efonidipine hydrochloride, oxytetracycline, oxyfedrine hydrochloride, oxprenolol hydrochloride, ondansetron hydrochloride, ecarazine hydrochloride, ephedrine hydrochloride, granisetron hydrochloride, clemizole hydrochloride, cloconazole hydrochloride, clonidine hydrochloride, clofedanol hydrochloride, chlordiazepoxide hydrochloride, chlorpromazine hydrochloride, cocaine hydrochloride, dicyclomine hydrochloride, dicethiamin hydrochloride, diphenylpyraline hydrochloride, diphenhydramine hydrochloride, diltiazem hydrochloride, daunorubicin hydrochloride, tulobuterol hydrochloride, tetracycline hydrochloride, delapril hydrochloride, doxycycline hydrochloride, doxorubicin hydrochloride, dopamine hydrochloride, dobutamine hydrochloride, tolazoline hydrochloride, tripelnnamine hydrochloride, naloxone hydrochloride, nalorphine hydrochloride, nicardipine hydrochloride, noscapine hydrochloride, vancomycin hydrochloride, histidine hydrochloride, pirarubicin hydrochloride, phenformin hydrochloride, buformin hydrochloride, flavoxate hydrochloride, protokylol hydrochloride, propranolol hydrochloride, promethazine hydrochloride, benexate hydrochloride betadex, picoperidamine hydrochloride, bufetolol hydrochloride, pethidine hydrochloride, maprotiline hydrochloride, mecamylamine hydrochloride, methylephedrine hydrochloride, methoxyphenamine hydrochloride, methdilazine hydrochloride, morphine hydrochloride, rilmazafone hydrochloride, levomepromazine hydrochloride, lomefloxacin hydrochloride, oxaprozin, oxymorphine, oxymetholone, oxendolone, ozagrel, ofloxacin, kanendomycin, carbazochrome sodium sulfonate, dry aluminum hydroxide gel, γ-orizanol, clomiphene citrate, sodium citrate, griseofulvin, glycyrrhizin, glipizide, glymidine sodium Krestin, cresol sodium sulfonate, clomipramine, clofibrate, cloperastine, chlorpropamide, ketoprofen, synthetic hydrotalcite, prednisolone sodium succinate, colchicine, chlormadinine acetate, cortisone acetate, prednisolone acetate, hexestrol acetate, betamethasone acetate, salicylamide, sodium salicylate, magnesium oxide, diazoxide, diazepam, digitoxin, diclofenac sodium, cyclophosphamide, sisomycin, cinoxacin, dibekacin, dipyridamole, diflunisal, betamethasone dipropionate, dextromethorphan hydrobromide, neostigmin bromide, pancuronium bromide, methscopolamine bromide, levorphanol tartrate, levallorphan tartrate, isosorbide nitrate, miconazole nitrate, cytosine arabinoside, cilostazol, cinnarizine, simvastatin, suprofen, sulpyrin, sulfazecin, sulfamethoxazole, sulfinpyrazone, sulindac, cefaclor, cefazolin, cephalexin, cephaloridine, defoxitin, cefotaxime, cefotiam, cefoperazone, cefsulodin, ceftizoxime, ceftibuten, cefmenoxime, cefmetazole, zotepine, thienamycin, thiotepa, ticarcillin, ticlopidine, tilactase, theophylline, tegafur, dexamethasone, testosterone, teceleukin, tetrahydrophyfuryl-5-fluorouracil, terfenadine, tolazamide, tranilast, trapidil, transexamic acid, trichlormethiazide, trifluoperazine, trimethoprim, tolfenamic acid, thromboplastin, naproxen, nitrazepam, nitroglycerin, nifedipine, noxiptilin, norethisterone, norfloxacin, baicalein, sodium p-aminosalicylate, haloperidol, panthenol, calcium pantothenate, picibanil, piperacillin, piroxicam, pindolol, phenytoin sodium, phenacetin, phenovalin, phenobarbital, fenoprofen calcium, chlorpromazine phenolphthalin, fenbufen, futraful, fumagillin, fluorouracil, fradiomycin, sodium flufenamate, pravastatin fluconazole, flutoprazepam, flurbiprofen, bleomycin, prostaglandins, progesterone, alclometasone dipropionate, dromostanolone propionate, propericiazine, flomoxef sodium, mometasone furoate, hexamethonium bromide, hexobendine, Bestatin, heparin sodium, beraprost, benzbromarone, pentolinium, fosfomycin, mitomycin C, chlorpheniramine maleate, trimipramine maleate, prochlorperazine maleate, levomepromazine maleate, caffeine anhydride, gabexate mesylate, dimethothiazine mesylate, proclorperazine mesylate, bromocriptine mesylate, mestranol, mesna, methotrexate, medazepam, pridinol methanesulfonate, methimazole, methyldopa, promethazine methylenedisalicylate, neostigmin methylsulfate, metoclopramide, metformin, metronidazole, menadione sodium hydrogensulfite, mepitiostane, mefenamic acid, betamethasone valerate, lipidomycin, codeine phosphate, erythromycin propionate lauryl sulfate, lisinopril, rifampicin, limaprost, atropine sulfate, salbutamol sulfate, cefpirome sulfate, terbutaline sulfate, bamethan sulfate, phenelzine sulfate, fradiomycin sulfate, morphine sulfate, dihydrocodeine phosphate, codeine phosphate, hexestrol phosphate, betamethasone phosphate sodium, levamisole, lentinan, loxoprofen sodium and rolitetracycline.

According to the method of the invention, high-quality hard capsules based on a water-soluble cellulose derivative can be produced under simple operational control.

The following experiment and examples are provided to illustrate the invention, and are not intended to limit the scope thereof.

EXPERIMENT

Hydroxypropyl methyl cellulose (HPMC, 75 kg) and potassium chloride (230 g) were added to 285 L of hot water (80° C.), following which the mixture was cooled and the viscosity at given temperatures was measured with a Brookfield-type viscometer (rotor No. 3, 6 rpm). After cooling to 27° C., the temperature was raised and the viscosity was similarly measured. When the temperature rose to 41° C., an aqueous solution obtained by adding 70 g of potassium chloride and 377 g of carrageenan to 39 kg of warm water was poured in and the viscosity was measured. The resulting mixture was allowed to cool, during which time the viscosity was similarly measured at predetermined temperature. The results are shown in Table 1 and FIG. 1.

TABLE 1

| Temperature (° C.) | Viscosity (mpa.s) | Appearance of liquid | Remarks |
| --- | --- | --- | --- |
| 60 | 500 | cloudy white | cooling |
| 55 | 1660 | cloudy white | cooling |
| 50 | 9160 | cloudy white | cooling |
| 45 | 18000 | cloudy white | cooling |
| 40 | 20950 | cloudy white | cooling |
| 27 | 7360 | clear | cooling |
| 30 | 5730 | clear | temperature rise |
| 35 | 5940 | clear | temperature rise |
| 41 | 6480 | clear | temperature rise |
| 41 | 3150 | clear | carrageenan addition |
| 38 | 3300 | clear | cooling |
| 36 | 4050 | clear | cooling |
| 35 | 4500 | clear | cooling |
| 32 | 14000 | clear | cooling |
| 30 | 13600 | clear | cooling |

EXAMPLE 1

Hydroxypropyl methyl cellulose (50 kg) was dispersed in 170 L of 80° C. water, then cooled to 25° C. to effect dissolution. The resulting solution was warmed to 45° C. and a solution prepared by dissolving 200 g of carrageenan in 20 L of 45° C. water was added thereto. Potassium chloride (276 g) was then added as a gelling aid, thereby giving a dipping solution.

Capsule were produced by inserting capsule-forming pins into the dipping solution, then drawing out the pins and drying at room temperature or 60° C.

EXAMPLE 2

Hydroxypropyl methyl cellulose (75 kg) was dispersed in 170 L of 80° C. water, then cooled to 19° C. to effect dissolution. The resulting solution was warmed to 41° C., and a solution prepared by dissolving 300 g of carrageenan in 30 L of 41° C. water was added thereto. Potassium chloride (300 g) was then added as a gelling aid, thereby giving a dipping solution.

Capsules were produced by inserting capsule-forming pins into the dipping solution, then drawing out the pins and drying at room temperature or 60° C.

EXAMPLE 3

Hydroxypropyl methyl cellulose (75 kg) was dispersed in 230 L of 80° C. water, then cooled to 25° C. to effect dissolution. The resulting solution was warmed to 41° C., and a solution prepared by dissolving 377 g of carrageenan in 39 L of 41° C. water was added thereto. Potassium chloride (300 g) was then added as a gelling aid, thereby giving a dipping solution.

Capsules were produced by inserting capsule-forming pins into the dipping solution, then drawing out the pins and drying at room temperature or 60° C.

EXAMPLE 4

Hydroxypropyl methyl cellulose (75 kg) was dispersed in 240 L of 80° C. water, then cooled to 25° C. to effect dissolution. The resulting solution was warmed to 41 ° C., and a solution prepared by dissolving 377 g of carrageenan in 39 L of 41° C. water was added thereto. Potassium chloride (300 g) was then added as a gelling aid, thereby giving a dipping solution.

Capsules were produced by inserting capsule-forming pins into the dipping solution, then drawing out the pins and drying at room temperature.

EXAMPLE 5

Hydroxypropyl methyl cellulose (75 g) was dispersed in 240 ml of 80° C. water, then cooled to 25° C. to effect dissolution. The resulting solution was warmed to 50° C. Another solution was prepared by dissolving 0.4 g of agar in 50 ml of 95° C. water and cooling to 50° C., after which it was added to the hydroxypropyl methyl cellulose solution, thereby giving a dipping solution.

Capsules were produced by inserting capsule-forming pins into the dipping solution, then drawing out the pins and drying at room temperature or 60° C.

EXAMPLE 6

Hydroxypropyl methyl cellulose (40 g) was dispersed in 130 ml of 80° C. water, then cooled to 20° C. to effect dissolution. The resulting solution was warmed to 41° C., and a solution prepared by dissolving 0.2 g of carrageenan in 30 ml of 41° C. water was added thereto. Potassium chloride (0.14 g) and ammonium acetate (0.2 g) were then added as gelling aids, thereby giving a dipping solution.

Capsules were produced by inserting capsule-forming pins into the dipping solution, then drawing out the pins and drying at room temperature or 60° C.

EXAMPLE 7

Hydroxypropyl methyl cellulose (75 kg) was dispersed in 244 L of 80° C. water, then cooled to 25° C. to effect dissolution. The resulting solution was warmed to 41° C., and a solution prepared by dissolving 327 g of carrageenan in 30 L of 41° C. water was added thereto. Potassium chloride (227 g) was then added as a gelling aid, thereby giving a dipping solution.

Capsules were produced by inserting capsule-forming pins into the dipping solution, drawing out the pins and holding them at room temperature for several seconds, then dipping the pins once again into the solution, drawing them out and drying at room temperature or 60° C.

EXAMPLE 8

Hydroxypropyl methyl cellulose (75 g) and potassium chloride (1.5 g) were dispersed in 230 ml of 80° C. water, then cooled to 25° C. to effect dissolution. The resulting solution was warmed to 45° C., and 1.6 g of carrageenan was added, thereby giving a dipping solution.

Capsules were produced by inserting capsule-forming pins into the dipping solution, then drawing out the pins and drying at room temperature or 60° C.

On the capsules produced in Examples 1 to 8, a solubility test was conducted under the standard conditions specified in The Japanese Pharmacopeia and using purified water warmed to 37±1° C. All of the capsules dissolved within 10 minutes.

What is claimed is:

1. A method of manufacturing hard capsules, characterized by comprising:
    dispersing a water-soluble cellulose derivative in hot water and cooling the dispersion to effect dissolution of the water-soluble cellulose derivative in the water,
    adding and dissolving a gelling agent in-the water-soluble cellulose derivative solution to give a capsule-preparing solution,
    dipping a capsule-forming pin into the capsule-preparing solution at a predetermined temperature, then
    drawing out the pin and inducing gelation of the capsule-preparing solution adhering to the pin.

2. The method of claim 1, wherein the water-soluble cellulose derivative is a cellulose ether substituted with alkyl and/or hydroxyalkyl groups.

3. The method of claim 2, wherein the cellulose ether is hydroxypropyl methyl cellulose.

4. The method of any one of claims 1 to 3, wherein the hot water in which the water-soluble cellulose derivative is dispersed has a temperature of at least 55° C., the dispersion is cooled to not higher than 35° C. and the capsule-preparing solution into which the capsule-forming pin is dipped has a temperature which is above 35° C., not more than 50° C., and precedes a sudden rise in solution viscosity.

5. The method of any one of claim 1, wherein the gelling agent is at least one member selected from the group consisting of carrageenan, tamarind seed polysaccharide, pectin, curdlan, gelatin, furcellaran, agar and gellan gum.

6. The method of any of claims 1, wherein the capsule-preparing solution additionally contains a gelling aid.

* * * * *